United States Patent
Eibs (10) Patent No.: US 11,607,122 B2
(45) Date of Patent: Mar. 21, 2023

(54) HANDS-FREE MECHANICAL MANIPULATION OF DUODENOSCOPE ELEVATOR DURING CLEANING

(71) Applicant: Medivators Inc., Plymouth, MN (US)

(72) Inventor: Thomas Edward Eibs, Minnetonka, MN (US)

(73) Assignee: Medivators Inc., Minneapolis, MN (US)

( * ) Notice: Subject to any disclaimer, the term of this patent is extended or adjusted under 35 U.S.C. 154(b) by 523 days.

(21) Appl. No.: 16/574,399

(22) Filed: Sep. 18, 2019

(65) Prior Publication Data

US 2020/0100665 A1   Apr. 2, 2020

Related U.S. Application Data

(60) Provisional application No. 62/739,538, filed on Oct. 1, 2018.

(51) Int. Cl.
| | | |
|---|---|---|
| *A61B 1/12* | (2006.01) | |
| *F16H 1/06* | (2006.01) | |
| *F16H 21/16* | (2006.01) | |
| *A61B 1/00* | (2006.01) | |
| *B08B 3/04* | (2006.01) | |
| *A61B 17/29* | (2006.01) | |
| *A61B 90/70* | (2016.01) | |

(52) U.S. Cl.
CPC .......... *A61B 1/123* (2013.01); *A61B 1/00133* (2013.01); *B08B 3/041* (2013.01); *F16H 1/06* (2013.01); *F16H 21/16* (2013.01); *A61B 17/29* (2013.01); *A61B 2090/701* (2016.02)

(58) Field of Classification Search
None
See application file for complete search history.

(56) References Cited

U.S. PATENT DOCUMENTS

| | | | |
|---|---|---|---|
| 5,271,379 A | | 12/1993 | Phan et al. |
| 5,490,015 A | * | 2/1996 | Umeyama ............. H02N 2/025 |
| | | | 359/813 |
| 5,573,494 A | * | 11/1996 | Yabe .................... A61B 1/0051 |
| | | | 600/106 |
| 5,931,833 A | | 8/1999 | Silverstein |
| 7,341,555 B2 | | 3/2008 | Dotawara et al. |
| 8,945,153 B2 | | 2/2015 | Surti |
| 2007/0226927 A1 | | 10/2007 | Suzuki et al. |

(Continued)

FOREIGN PATENT DOCUMENTS

| | | |
|---|---|---|
| JP | 3387357 | 3/2003 |
| JP | 2004248800 | 9/2004 |

(Continued)

*Primary Examiner* — Cristi J Tate-Sims
(74) *Attorney, Agent, or Firm* — Renner, Otto, Boisselle & Sklar LLP (57) ABSTRACT

An endoscope cleansing accessory is described for use with an automatic endoscope reprocessing (AER) apparatus which utilizes the motive force provided by a flowing cleansing fluid already within the AER to actuate an actuator wheel of the endoscope during the cleansing process. The movement or actuation of the actuator wheel during cleansing in turn imparts a back and forth motion to an elevator platform or forceps raiser within the endoscope to loosen tissue and other particles that are then flushed out by the flowing cleansing fluid.

11 Claims, 9 Drawing Sheets

(56) References Cited

U.S. PATENT DOCUMENTS

| | | | |
|---|---|---|---|
| 2014/0155696 A1 | 6/2014 | Sakata | |
| 2016/0089125 A1* | 3/2016 | Morimoto | A61B 1/00098 600/107 |
| 2017/0258460 A1 | 9/2017 | Zimmon | |
| 2019/0150710 A1* | 5/2019 | Nakazato | A61B 1/126 |

FOREIGN PATENT DOCUMENTS

| | | |
|---|---|---|
| JP | 2004254806 | 9/2004 |
| JP | 2009183470 | 8/2009 |
| WO | 2016103247 | 6/2016 |

\* cited by examiner

HANDS-FREE MECHANICAL MANIPULATION OF DUODENOSCOPE ELEVATOR DURING CLEANING

PRIORITY CLAIM

This application claims priority to and the benefit of U.S. Provisional Application with Ser. No. 62/739,538 filed on Oct. 1, 2018, entitled HANDS-FREE MECHANICAL MANIPULATION OF DUODENOSCOPE ELEVATOR DURING CLEANING, which is herein incorporated by reference in its entirety.

FIELD AND BACKGROUND

The invention relates generally to cleaning devices and disinfection systems for endoscope devices and other surgical equipment.

Endoscopic devices have been commonly used for various procedures, including the examination and inspection of the interior of body organs, joints or cavities and the body's passageways. An endoscopic procedure may be used to diagnose various conditions by close examination of internal organ and body structures and may also guide therapy and repair, such as the removal of torn cartilage from the bearing surfaces of a joint. A biopsy, a procedure involving tissue sampling for pathologic testing, may also be performed under endoscopic guidance or for diagnostic procedures, including contrast imaging of biliary or pancreatic ducts. Endoscopes are also frequently used in procedures for retrieving gallstones that exist in the common bile duct and elsewhere.

Typically, these treatments are performed in the pancreatic duct, bile duct, and the hepatic duct by positioning the distal end of an endoscope in the vicinity of the duodenal papilla. Once the endoscope is in place, a wire guide is delivered to the target anatomy via the working channel of the endoscope. In order to guide the wire guide (or other medical instruments) out of the working channel of the endoscope, a rigid elevator or forceps raiser is typically used to orient or deflect the distal end of the wire guide. When the distal end of the wire guide is oriented, the wire guide is inserted into the target anatomy. At this point in the procedure, a catheter or similar treatment instrument can be passed over the wire guide either in a conventional over-the-wire style to the target anatomy.

Additionally, other medical devices such as catheters are disposed through the working channel of an endoscope for various treatments and procedures wherein an elevator is used to position the device at a target location in the patient anatomy. Current endoscopes with elevators simply actuate or lift the elevator relative to the distal tip of an insertion tube to move the device from one location to another. Even while use of endoscopic instruments is minimally invasive, without proper care, they can still transmit disease. It is necessary that endoscopes be well cleaned and disinfected or sterilized after each use to prevent transfer of potentially dangerous agents between patients. Endoscopes will also often operate in what can be considered a wet environment or other environment where body fluids are in contact with the exterior of the endoscope which is generally a form of rubber tubing. Cleaning and sterilization systems also often utilize liquids in cleaning. Because an endoscope's sophisticated design uses a high number of components which can be adversely affected by moisture, generally an endoscope will be sealed from external fluid invasion by having its components sealed inside the flexible plastic or rubber sleeve. Components which are not sealed during use are alternatively sealed by caps during cleaning as the entire instrument can be inserted in liquid during the cleaning process. To clean endoscopes between procedures, generally the endoscope is first disconnected from associated computer apparatus, is wiped down and open channels are suctioned and washed to remove most of the material on the scope. The scope is then sent to be cleaned. As cleaning requires specific immersion or saturation of the endoscope with liquid materials, it is important that the scope be checked for leaks prior to this cleaning; otherwise a leak could admit cleaning materials and damage the endoscope. Traditionally, leaks were tested for by a technician who would access the internal structure of the endoscope, and if a leak was detected, connect an air source and introduce air to raise the internal pressure of the scope above the ambient to inhibit fluid invasion during cleaning and prior to repair.

However, with each use of the endoscope and elevator assembly, cleaning and disinfection of the internal working parts becomes more challenging requiring more mechanical manipulation and actuation of the elevator assembly or forceps raiser with disinfecting solutions to ensure residual particles are removed and do not remain lodged therein prior to placement of the endoscope in an AER for final cleaning and disinfecting. Such manual mechanical manipulation of the elevator assembly in the endoscope is time consuming and labor intensive causing delays in surgical schedules or forcing hospitals and ambulatory surgical centers to increase their investment in endoscopes to ensure there are enough available to run an efficient surgical center.

Therefore there is a need for an endoscope cleaning system that will improve cleaning and disinfection outcomes without increasing capital costs due to investments in additional endoscopic equipment or labor costs due to longer manual cleaning times of endoscopes.

SUMMARY

It would be advantageous to reduce labor intensive and time consuming endoscope cleansing processes of endoscopes while improving disinfection outcomes and achieving reduced overall cleaning throughput times without substantially increasing the capital costs of an end user. The invention relates generally to devices and systems for cleaning and disinfecting elevator platforms or forceps raiser mechanisms of endoscope devices. The various embodiments described herein provide an advantage over the prior art devices and systems for hands-free cleaning of the internal mechanical elevator or forceps raiser mechanisms of endoscopes by harnessing motive energy from the fluid flow within an automatic endoscope reprocessor (AER) apparatus to actuate a reciprocating mechanism within the endoscope that will move the elevator platform up and down while the endoscope is being cleaned/disinfected in the AER. In essence, motive energy of the fluid flow (e.g., water and cleansing fluid) within the AER is converted or translated into a reciprocating linear motion to actuate the actuator lever on the duodenoscope. Advantageously, the fluid flow force provided by the AER equipment is used to not only drive the elevator actuator lever during cleaning but also the basic concept of harnessing the fluid flow of the AER as a motive energy source to drive other mechanisms to clean or scrub other internal conduits and parts of the endoscope.

In one example embodiment, a connecting rod is connected on one end to the actuator lever on the duodenoscope while the other end of the connecting rod is connected to a water wheel drive assembly that is driven radially by the fluid flow within the AER. As the water wheel and reduction gears turn the connecting rod imparts an actuating motion on the actuator lever on the duodenoscope. In a related embodiment, a turbine drive mechanism drives the actuator lever of the elevator in the duodenoscope by subjecting a turbine member to the fluid flow of the AER either axially (or radially) and then transitioning through a reduction stage to an actuator wheel connected to a rod coupled to a scope elevator actuator.

In another example embodiment, a solenoid drive mechanism uses fluid flow from the AER to convert same to electric current to then drive a solenoid that actuates the actuator lever on the duodenoscope. In yet another example embodiment, an impact drive (impact sprinkler-type) mechanism is configured and connected to the actuator lever of the duodenoscope, whereby the impact head is in the stream of fluid flow and moves a ratcheting member coupled to the actuator lever of the elevator platform.

In one example embodiment, there is provided an endoscope accessory assembly for use with an endoscope during processing with a cleansing fluid in an automatic endoscope reprocessing apparatus, the endoscope having an actuator wheel rotatable axially about a center axis within the endoscope so as to operate an elevator platform or forceps raiser device located at a distal end of the endoscope, the endoscope accessory assembly including a linear wheel coupler disposed on a surface of the actuator wheel having a first end engaged with an outer surface of an external gear member, the linear wheel coupler configured to rotate the actuator wheel axially as the linear wheel coupler moves laterally across the external gear member. The endoscope accessory also including a gear reduction assembly mechanically coupled at an inside surface of the external gear member of the linear wheel coupler, the gear reduction assembly configured to impart a lateral back and forth motion to the linear wheel coupler and a fluid wheel coupled to the gear reduction assembly opposite the linear wheel coupler, the fluid wheel having a plurality of capture fins disposed about a peripheral edge of the fluid wheel and configured to rotate axially in a direction of the cleansing fluid flowing across the peripheral edge of the fluid wheel, the fluid wheel imparting a rotational force on the gear reduction assembly from a motive force generated by the cleansing fluid flow, wherein the lateral back and forth motion on the linear wheel coupler translates to an opening and closing of the elevator platform by the actuator wheel within the endoscope during endoscope reprocessing.

In another example embodiment, there is provided an endoscope accessory assembly for use with an endoscope during processing with a cleansing fluid in an automatic endoscope reprocessing apparatus, the endoscope having an actuator wheel rotatable axially about a center axis within the endoscope so as to operate an elevator platform or forceps raiser device located at a distal end of the endoscope, the endoscope accessory assembly including a direct wheel coupler having a first coupler end configured to engage the actuator wheel and to rotate the actuator wheel axially upon actuation; a gear assembly mechanically coupled to a second coupler end of the direct wheel coupler, the gear assembly configured to impart a rotational force to the direct wheel coupler. The endoscope accessory also including a fluid turbine member coupled to the gear assembly opposite the direct wheel coupler, the fluid turbine member having a plurality of blades disposed within a body or housing of the fluid turbine member and configured to rotate perpendicularly to a direction of the cleansing fluid flowing across the plurality of blades, the turbine member imparting a rotational force to the gear assembly from a motive force generated by the cleansing fluid flow, wherein the rotating motion on the direct wheel coupler translates to an opening and closing of the elevator platform by the actuator wheel within the endoscope during endoscope reprocessing.

In another embodiment, there is provided an endoscope accessory assembly for use with an endoscope during processing with a cleansing fluid in an automatic endoscope reprocessing apparatus, the endoscope having an actuator wheel rotatable axially about a center axis within the endoscope so as to operate an elevator platform or forceps raiser device located at a distal end of the endoscope, the endoscope accessory assembly including a fluid turbine member having a plurality of blades disposed within a body of the fluid turbine member and configured to rotate perpendicularly to a direction of the cleansing fluid flowing across the plurality of blades, the turbine member imparting a rotational force to a connecting shaft or rod protruding from a center axis of the turbine member from a motive force generated by the cleansing fluid flow. The endoscope accessory also including a direct current (DC) generator coupled to the connecting shaft or rod from the fluid turbine member, the DC generator having two electrical leads for transmitting DC current generated by the generator. Further, the endoscope accessory includes a solenoid device assembly including a housing and a plunger rod disposed therein and protruding partially therefrom, the plunger rod having a spring member located concentrically about the plunger rod and adjacent the housing, the solenoid device electrically connected to the two electrical leads of the DC generator and configured to move the plunger rod in and out of the housing upon being energized by the DC current, wherein the movement of the plunger rod along with the spring member impart an actuating force on the actuator wheel of the endoscope controlling the elevator or forceps device during endoscope reprocessing.

In yet another example embodiment, there is provided an endoscope accessory assembly for use with an endoscope during processing with a cleansing fluid in an automatic endoscope reprocessing apparatus, the endoscope having an actuator wheel rotatable axially about a center axis within the endoscope so as to operate an elevator platform or forceps raiser device located at a distal end of the endoscope, the endoscope accessory assembly including an impact head assembly having an impact head member disposed on a connecting shaft or rod member in a T-configuration, the connecting shaft or rod having a spring member located concentrically about a lower portion of the rod, the spring member configured to allow a predetermined axial rotational movement of the impact head assembly upon the impact head member being subjected to a rotational force from a motive force generated by the cleansing fluid flow. The endoscope accessory also including a ratchet member operatively coupled with the connecting rod of the impact head assembly, the ratchet member including a predetermined number of indentations configured to engage a pin protruding laterally from the connecting rod that maintains the impact head member in a first position, the pin advancing progressively through the indentations as the impact head member is subjected to the motive force until the indentations terminate and the ratchet member releases the impact head assembly such that the impact head member moves to a second position, the rotational movement of the impact head assembly to the second position imparting a rotational force on a distal end of the connecting rod. Further, the endoscope accessory including and a direct wheel coupler having a first coupler end configured to engage the connecting rod and a second end configured to engage the actuator wheel and rotate the wheel axially upon receiving an actuation force, wherein the movement of the connecting rod along with the spring member impart an actuating force on the actuator wheel of the endoscope controlling the elevator or forceps device during cleansing of the endoscope, wherein the rotating motion on the direct wheel coupler translates to an opening and closing of the elevator platform by the actuator wheel within the endoscope during endoscope reprocessing.

In yet another example embodiment, there is provided a method of cleaning an endoscope during endoscope reprocessing, the endoscope having an actuator member rotatable axially about a center axis within the endoscope so as to operate an elevator platform or forceps raiser device located at a distal end of the endoscope, the cleaning method comprising the steps of engaging with a first end of a manipulator assembly the actuator member of the endoscope, the manipulator assembly configured to move the elevator platform with the actuator member in a cantilevering motion. Next, the method includes locating a second end of the manipulator assembly in a flow path of a cleansing fluid; initiating flow of the cleansing fluid with a flow rate and volume sufficient to create a motive force. Further, the method includes engaging the fluid flow and motive force of the cleansing fluid with the second end of the manipulator assembly so as to continuously move the elevator platform or forceps raiser in the cantilevering motion.

In the various embodiments described herein, bands or belt assemblies are used as substitutes for the gear assemblies for transferring or translating force or movement.

The invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

DETAILED DESCRIPTION OF THE INVENTION

Following are more detailed descriptions of various related concepts related to, and embodiments of, methods and apparatus according to the present disclosure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

Figure 1A:
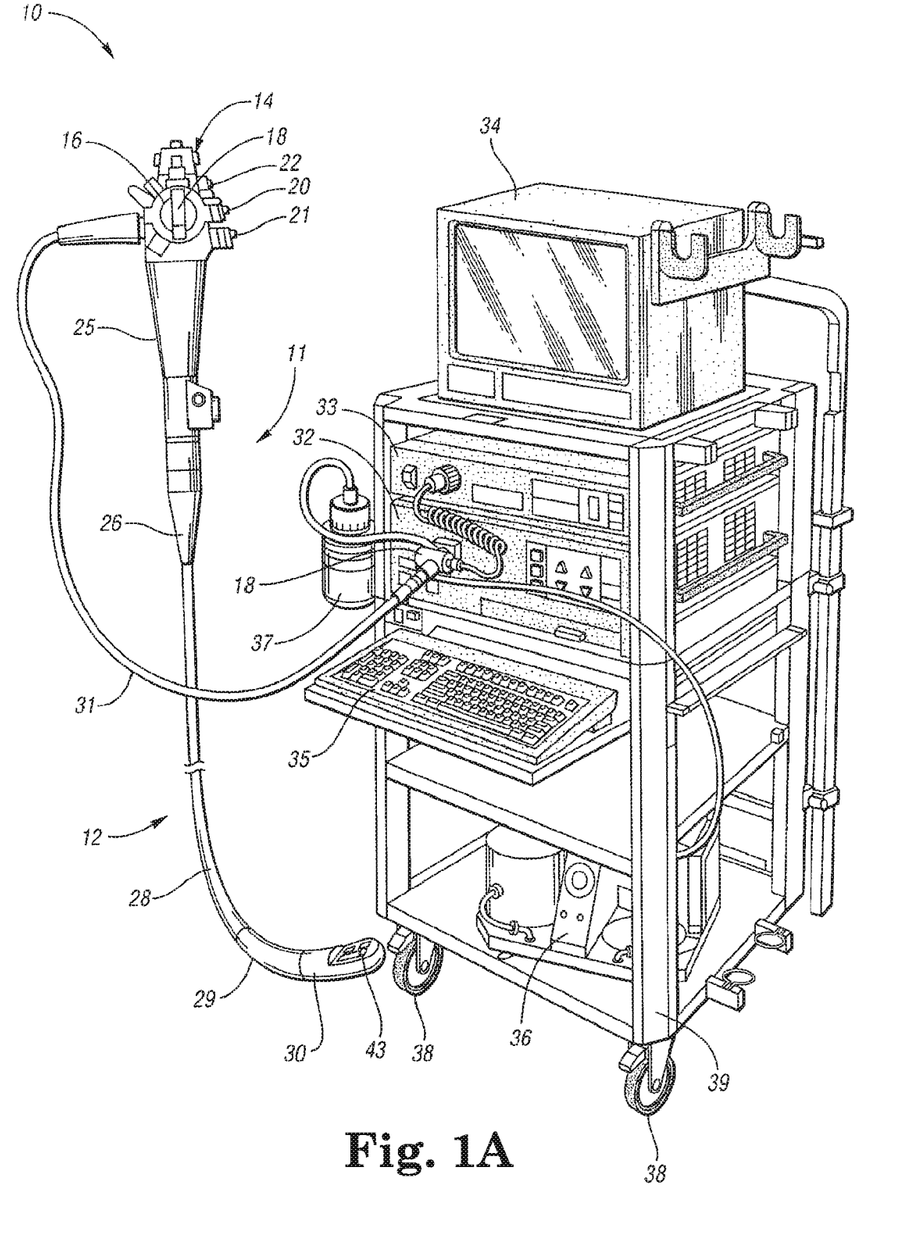
FIGS. 1A, 1B and 1C are perspective views of a prior art endoscopic system including a standard endoscope, a standard endoscope located in a tray for processing in an automatic endoscope processing machine for cleaning and disinfecting an endoscope, and a distal end of the endoscope illustrating an elevator or forceps raiser, respectively.
Figure 1B:
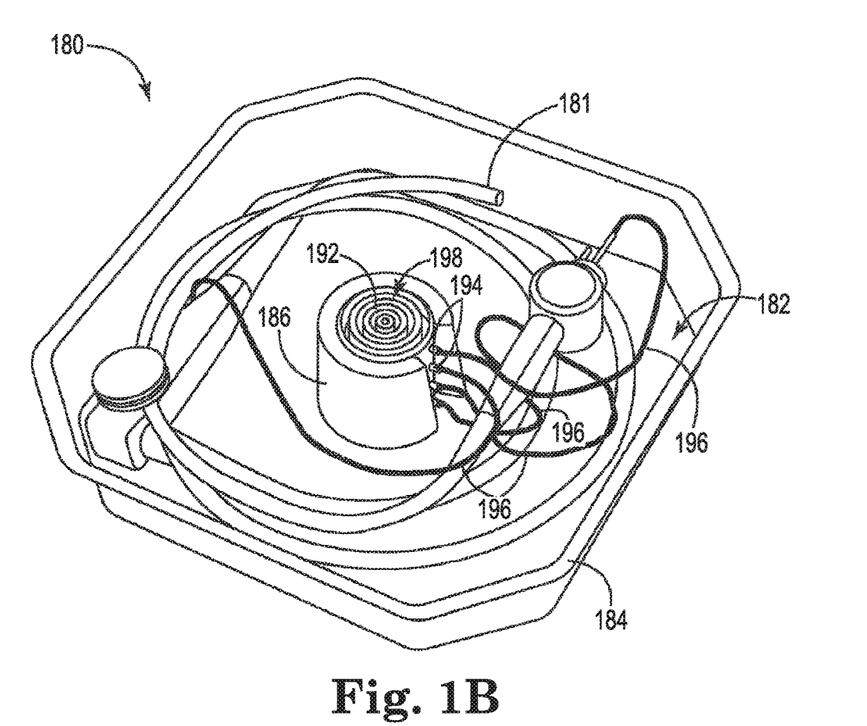
Figure 1C:
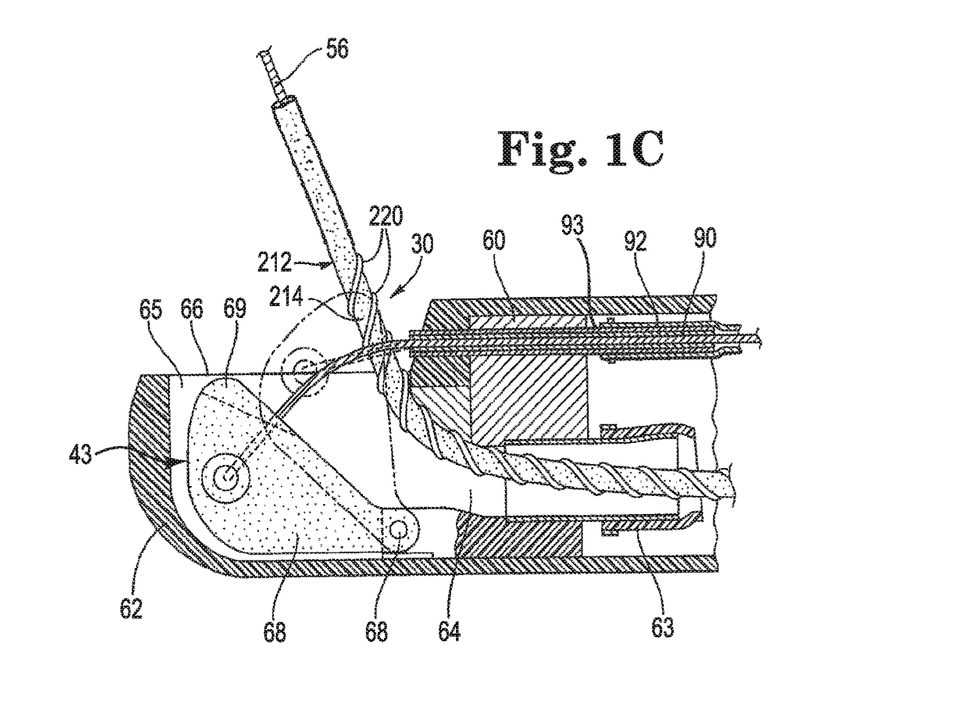

Referring to the figures, FIGS. 1A-1C are perspective views of a prior art endoscopic system 10 including a standard endoscope, a standard endoscope located in a tray for processing in an automatic endoscope processing machine for cleaning and disinfecting an endoscope, and a distal end of the endoscope illustrating an elevator or forceps raiser 69, respectively. In particular, FIG. 1A illustrates an endoscopic system 10 comprising an endoscope 11 with an insertion tube 12 to be inserted into a body cavity for various endoscopic procedures. The insertion tube 12 has a channel port through which endoscopic units may be disposed. In one embodiment, endoscopic units disposed in one of the ports may include one embodiment of an elevator or forceps raiser having a distal tip. Endoscope 11 further includes a control system 14 that is in mechanical and fluid communication with the insertion tube 12 and controls the insertion tube 12 and endoscopic parts disposed therein. Control system 14 includes first and second control knobs 16, 18. The control knobs 16, 18 are in mechanical communication with the insertion tube 12 and allow the physician to control and guide insertion tube 12 through vessels and cavities of a patient. The control system 14 further includes valve switches (e.g., suction valve 20, air/water valve 21, camera valve 22), each of which are in communication with one of the channel ports of the insertion tube 12. For example, the suction valve switch 20, when activated, allows a vacuum from a suction source through a suction channel port for suctioning unwanted plaque and debris from the patient. In one example, the distal end of the insertion tube 12 is inserted, rectally or orally, to a predetermined endoscopic location within a patient. An endoscope cover or coating 63 disposed about elevator 69 at endoscope tip 30 the distal tip of endoscope 11 helps to reduce the risk of tearing or scraping of patient tissue by the wire guide.

In this embodiment, the insertion tube 12 comprises an operating portion 25 connected to the control system 14 and extending to an insertion protecting member 26. A control system 14 is connected to the operating portion 25 and is configured to control the insertion tube 12. In this embodiment, the insertion tube 12 is composed of components that include a flexible tube 28, a flexure 29 connected to the flexible tube 28, and an endoscope tip 30 connect to the flexure 29. A universal cord 31, on one end, is connected and in communication with the control system 14. On the other end, the cord 31 has a connector 18 attached thereto. The connector 18 is in communication to a light guide tube and electrical contact, and is connected to a light source apparatus 32 and an image processing apparatus 33 (external devices). These external devices may include a monitor 34, an input keyboard 35, a suction pump apparatus 36, irrigation bottle 37, and other suitable apparatus that are installed on a rack 39 equipped with rollers 38.

Referring now to FIG. 1B, there is illustrated a perspective view of an embodiment of a tray 180 for retaining an endoscope 181 (or any other medical device) 181 before, during, and after decontamination of endoscope 181 in this example by an automatic endoscope reprocessor (AER) of the type described in U.S. Pat. No. 8,821,807 and sold by Medivators, a division of Cantel Medical, based in Minneapolis, Minn. In this example, tray 80 includes a front cover layer 182, a container 184, and a connector support 186, however in other AERs endoscope 181 can be placed directly in the cleansing bin.

To facilitate connection of the endoscope or other medical device to a fluid control valve, connector support 186 is configured to retain a connector 192 that includes one or more connection interfaces 194 that may be coupled to channels or ports of endoscope 181. A conduit 196 is connected to each of the connection interfaces 194 on the connector 192 at one end and to endoscope 181 at the other end and may also be coupled to channels in the endoscope to provide a fluid path from between the connector 192 and the channels. The connector 192 includes openings 198 that connect the connection interfaces 194 to the top of the connector 192. In this example, once the AER apparatus is closed, a cleansing fluid floods tray or chamber 180 such that the entire device 181 is bathed in the disinfectant and the cleansing fluid flows through the interior channels of the endoscope with the goal being that tissue, blood, mucus and other bodily fluids are flushed out of the endoscope and the device is sanitized. One of the challenges recognized herein is the possibility of tissue or other debris remaining in an elevator platform or forceps raiser of the endoscope. The inner workings of the elevator will be described herein below to assist in the understanding of the benefits of the inventive concepts taught herein.

Referring now to FIG. 1C, the is illustrated a side view of a typical elevator or forceps raiser device 69 used to move the distal end of the endoscope at tip 30 to improved viewing or for collecting biopsies. Endoscope tip 30 includes a cuff 60 as the main body of the tip 30, and a sleeve or cover 62 that covers the perimeter of the cuff 60. As shown, the cover 62 is formed using a nonconductive member such as any suitable polymeric material, e.g., high density polyethylene or polypropylene. In this embodiment, the cover 62 is attached to the cuff 60 by any suitable means, e.g., by adhesive bonding. The cuff 60 is disposed adjacent the working channel 63, which acts as a passageway for the insertion of the medical instrument, e.g., wire guide or catheter. In this embodiment, a channel is formed through the tip 30 such that the tip opening of the treatment instrument is able to be disposed through the channel opening. In this example, an elevator wire 90 is connected to an elevator 43 extends through a guide tube 92 and a guide pipe 93 connected to the guide tube 92. The elevator wire 90 is in mechanical communication with the control system 14 so that manipulations at the control system 14 result in movement of the elevator wire 90 relative to the endoscope. FIG. 1C depicts (in phantom) movement of elevator 43 when the elevator wire 90 is actuated at the control system 14, moving the position of the elevator 43 about the elevator turning support 68 as the elevator wire 90 is retracted or pulled. In this embodiment, the elevator 43 is moved about the elevator turning support 68 by manipulating or actuating the control system 14 (or an actuator wheel or other actuator member) to pull or retract the elevator wire 90.

As discussed above, one of the challenges in cleansing and disinfecting an endoscope includes removing human debris and tissue from the elevator. Before placing the endoscope in an AER apparatus, hospital personnel manually clean the endoscope in a detergent solution and scrub the external surfaces of the endoscope, manually actuating or manipulating the actuator wheel or actuator member that moves or cantilevers the elevator (or forceps raiser) housed within the endoscope in an attempt to loosen human debris and particles that may have gotten lodged in the elevator assembly prior to placing the endoscope in the AER. However, once the endoscope is inside the AER it would be desirable to find a method and mechanism that can manually manipulate the elevator while it is in the AER. Further, harnessing the motive force of the flow of cleansing fluid would also be an advantage in actuating the elevator mechanism or any other internal mechanism of a medical appliance or device.

There is disclosed a method and various manipulator assemblies in FIGS. 2A-5B that move the elevator or forceps raiser while the endoscope is in the AER while using the motive force of the cleansing fluid, with a sufficient flow rate and volume, within the AER to power the manipulator assembly. In a related embodiment, a cleaning gas with a sufficient flow rate and volume to create the motive force is also an option. Referring generally to FIGS. 2A-5B, there is provided a method of cleaning an endoscope during endoscope reprocessing, in this example embodiment endoscope 12 which has an actuator member, similar to actuator wheel but not limited to a wheel, that is rotatable axially about a center axis within endoscope 12 so as to operate an elevator platform 43 or forceps raiser device located at a distal end of the endoscope. The cleaning method includes the steps of engaging with a first end of a manipulator assembly (manipulator assemblies 300, 400, 500 and 600 described in more detail in FIGS. 2A-5B) the actuator member of the endoscope, the manipulator assembly configured to move the elevator platform 43 with the actuator member (or wheel) in a cantilevering motion. Next, a second end of the manipulator assembly is located in a flow path of a cleansing fluid and then the flow of the cleansing fluid is initiated with a flow rate and volume sufficient to create a motive force. The method then includes engaging the fluid flow and motive force of the cleansing fluid with the second end of the manipulator assembly so as to continuously move the elevator platform or forceps raiser in the cantilevering motion. In a related embodiment, the actuator member is an actuator wheel coupled to the elevator or forceps raiser. In a related embodiment, the cleansing method uses one of manipulator assembly including a fluid wheel assembly 300 and a fluid turbine member assembly 500. In yet another embodiment, the method uses manipulator assembly that includes a solenoid device assembly 600. In yet another related embodiment the method uses the manipulator assembly that uses an impact head assembly 400.

Referring now to FIGS. 2A-2E illustrate a perspective, side and front views of a water wheel or turbine drive assembly (mechanical manipulator assembly) 300 and output shaft configurations that are driven perpendicular to a direction of rotation of a shaft by a cleansing fluid flow 306 within the AER apparatus (not shown), when an endoscope 302 is being cleaned in the AER, which in turn drives an actuator lever 304 of the elevator in the duodenoscope (or endoscope) which controls an elevator platform or forceps raiser, such as elevator 43. In this example embodiment, the endoscope has an actuator wheel 304 rotatable axially about a center axis within the endoscope 302 so as to operate the elevator platform or forceps raiser device located at a distal end of the endoscope 302. In this example embodiment, the endoscope or manipulator accessory assembly 300 includes a linear wheel coupler assembly 310 (two bars 310b and 310C, in this embodiment) disposed on and engaging a surface 303 of actuator wheel 304 having a first end 310A engaged with an outer surface 312A of an external gear member 312. Linear wheel coupler 310 is configured to rotate actuator wheel 304 axially (or actuator mechanism that cantilevers the elevator) as linear wheel coupler 310 moves laterally across external gear member 312. In related embodiment illustrated in FIG. 2E, a single coupling rod 310D coupled at surface 312A is used to manipulate or turn actuator wheel 304 at surface 303 using a linear motion of 310D (arrow) when gear member 312 is moved back and forth (see back/forth arrow).

Figure 2A:
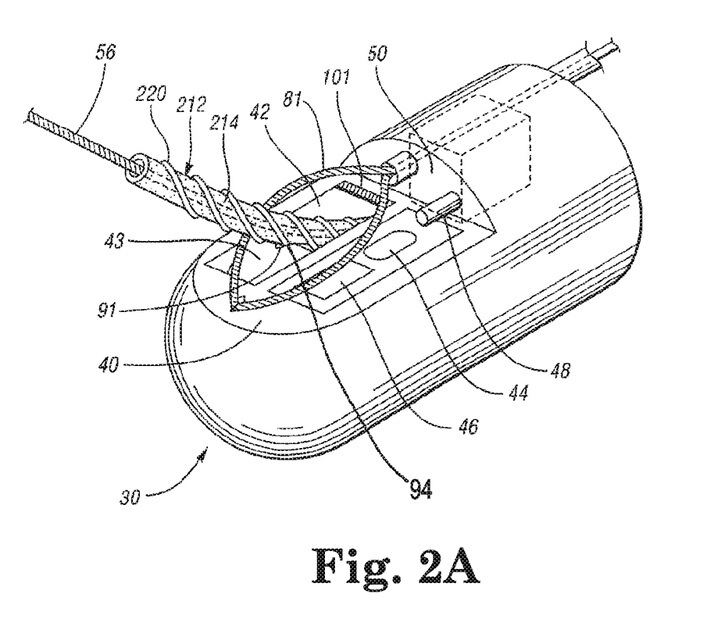
FIGS. 2A-2E illustrate perspective, side and front views of a water wheel or turbine drive assembly, and output shaft configurations, which are driven perpendicular to a direction of rotation of a shaft by the fluid flow within the AER which in turn drives an actuator lever of the elevator in the duodenoscope which controls an elevator platform or forceps raiser.
Figure 2B:
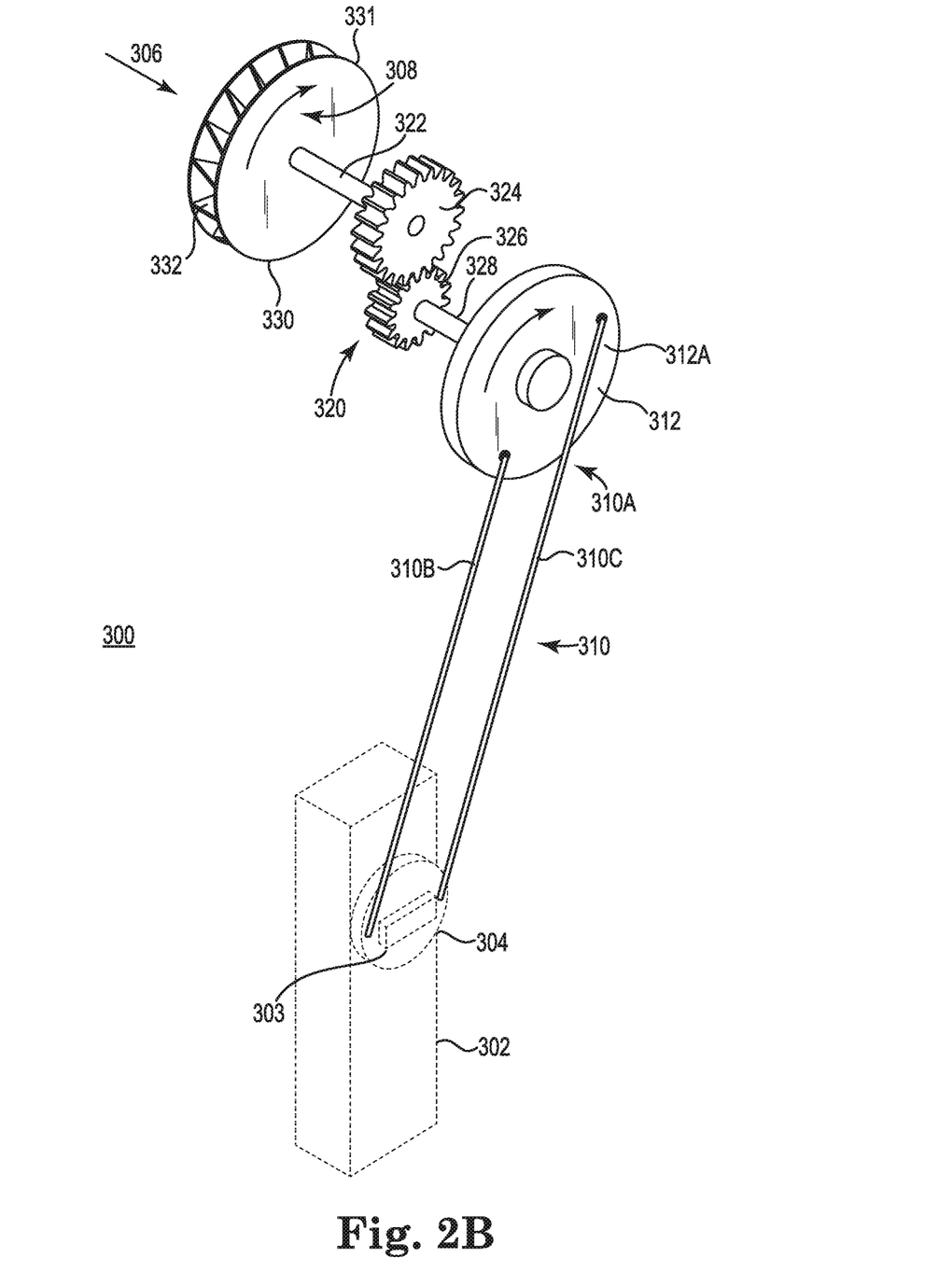

In this example embodiment, manipulator assembly 300 further includes a gear reduction assembly 320 that is mechanically coupled at an inside surface of external gear member 312 of linear wheel coupler 310, gear reduction assembly 320 configured to impart a lateral back and forth motion to linear wheel coupler 310.

A fluid wheel 330 is coupled to gear reduction assembly 320 opposite linear wheel coupler 310, fluid wheel 330 having a plurality of capture fins 332 disposed about a peripheral edge 331 of fluid wheel 330 which rotate axially in a direction perpendicular to the cleansing fluid flowing 306 across a face of fluid wheel 330, fluid wheel 330 then imparting a rotational force 308 on gear reduction assembly 320 from a motive force generated by cleansing fluid flow 306, wherein the lateral back and forth motion on linear wheel coupler 310 translates to an opening and closing of the elevator platform by actuator wheel 304 within the endoscope 302 during endoscope reprocessing. Optionally, wheel coupler 310 has one connect bar versus that which is illustrated in FIG. 2A. In one example embodiment, gear reduction assembly 320 includes a connecting rod or shaft assembly 322 coupled from a first gear 324 of the gear reduction assembly to a surface of fluid wheel 330, connecting shaft assembly 322 transferring rotational motion to first gear 324 of the gear reduction assembly. In this example embodiment, gear reduction assembly includes a second gear 326 coupled to a connecting shaft or rod 328 that is also connected to external gear 312.

Figure 2C:
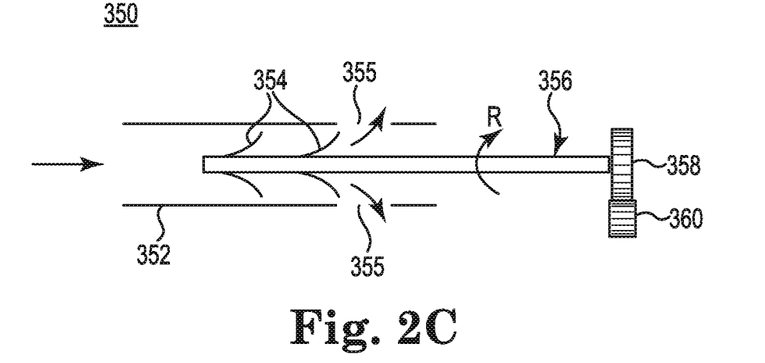
Figure 2D:
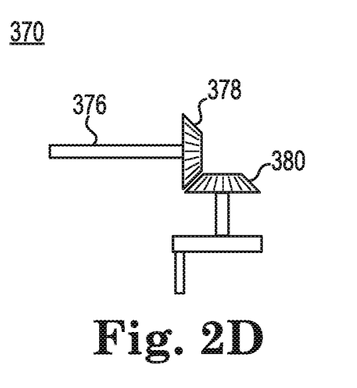
Figure 2E:
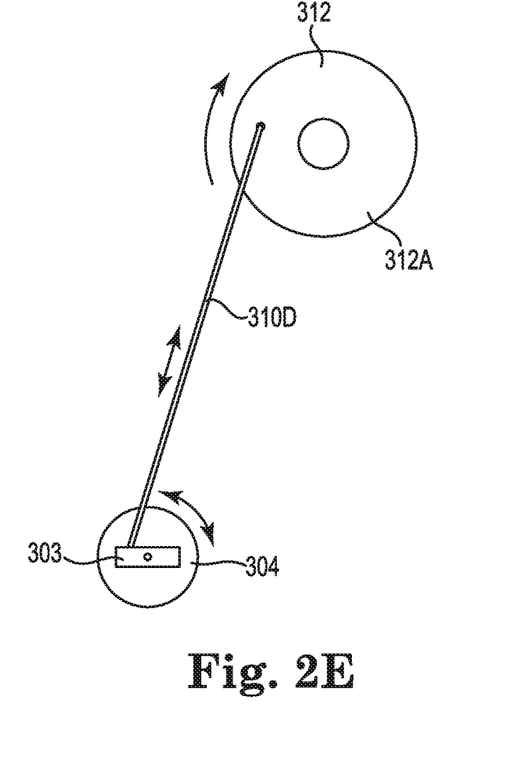

FIGS. 2C and 2D illustrate other output shaft embodiments that utilize aforementioned perpendicular fluid flow of the cleansing fluid in the AER to drive the output shaft in a parallel drive train 350 and an offset drive configuration 370, respectively. With respect to configuration 350, a turbine assembly includes a housing 352 with a plurality of blades 354 disposed on an output shaft 356 with a gear member 358 disposed thereon. As fluid flows (in the direction of the arrow) through housing 352 and catch blades 354 and flows out of a series of outlets 355, shaft 356 rotates in a direction R that is parallel to the fluid flow, thereby turning a gear 360 disposed on a distal end of shaft 358. Gear 360 forms part of a parallel drive train that is then coupled to a gear reduction assembly described in FIG. 2B. Similarly, offset drive train 370 is coupled to shaft 356 on one end and is engaged to gear 362 on the other end in an offset configuration, thereafter being coupled to the elevator and wheel actuator via the gear reduction assembly described in FIG. 2B.

Figure 3A:
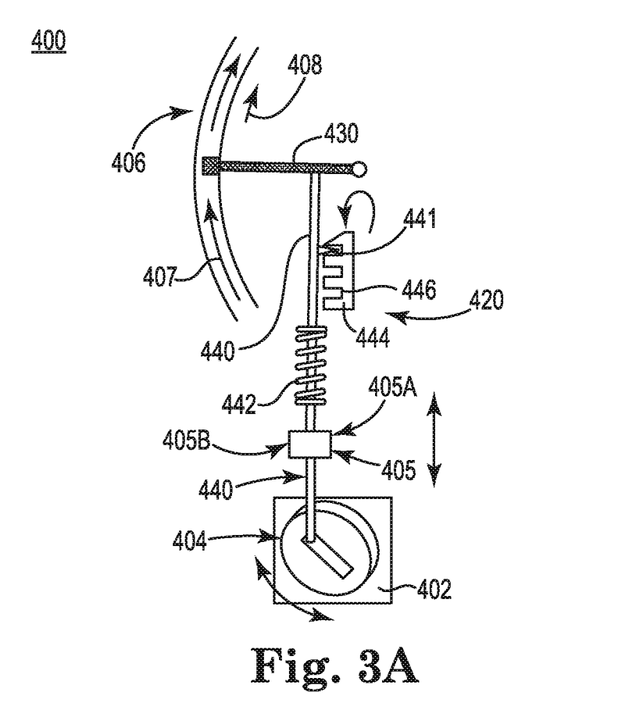
FIGS. 3A-3B illustrate front views of impact drive (impact sprinkler-type) mechanisms connected to the actuator lever of the duodenoscope, whereby the impact head is in the stream of fluid flow and moves a ratcheting member coupled to the actuator lever of the elevator platform having movement in one of a linear/translational or rotational direction for actuating the actuator lever.
Figure 3B:
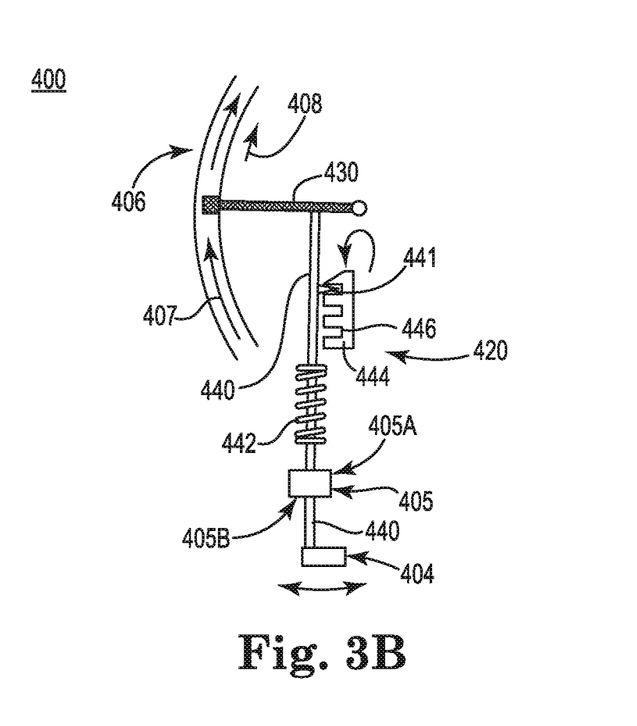

Referring now to FIGS. 3A-3B, there is illustrated front views of an impact drive (impact sprinkler-type) manipulator mechanism or assembly 400 connected to an actuator lever 404 of the endoscope or duodenoscope 404. In operation, an impact head 430 of manipulator assembly 400 is located in a stream 406 of the cleansing fluid flow and moves a ratcheting member 444 coupled to actuator lever 404 of the elevator platform to move the elevator while it is being cleaned. In this example embodiment, manipulator or endoscope accessory assembly 400 includes an impact head assembly 420 having an impact head member 430 disposed on a connecting rod member 440 in a T-configuration, connecting rod 440 includes a spring member 442 located concentrically about a lower portion of the rod 440, spring member 442 configured to allow a predetermined axial rotational movement, shown in FIG. 3B (or linear/translational as shown in FIG. 3A), of impact head assembly 420 upon impact head member 430 being subjected to a rotational force 408 (or lifting force for FIG. 3A) from a motive force 407 generated by the cleansing fluid flow 406.

A ratchet member 444 operatively coupled with connecting rod 440 of impact head assembly 420, including a predetermined number of indentations 446 that engage a pin 441 protruding laterally from connecting rod 440 that maintains impact head member 430 in a first position, pin 441 advancing progressively through each of indentations 446 as impact head member 430 is subjected to motive force 408 until indentations 446 terminate and ratchet member 444 releases impact head assembly 420 such that impact head member 430 moves to a second position, the rotational movement shown in FIG. 3B (or linear movement shown in FIG. 3A) of impact head assembly 430 moving to the second position imparting a rotational force on a distal end of connecting rod 44 (or imparting a linear or vertical force, FIG. 3A). A direct wheel coupler 405 having a first coupler end 405A configured to engage connecting rod 440 and a second end 405B configured to engage actuator wheel 404 and rotate wheel 404 axially upon receiving an actuation force in FIG. 3B (arrow) or linearly moving wheel 404 up (see arrow) in FIG. 3A when rod 440 is moved up, wherein the movement of connecting rod 440 along with spring member 442 impart an actuating force on the actuator wheel 404 of endoscope 402 controlling the elevator or forceps device during cleansing of endoscope 402.

In FIG. 3B, connecting rod 440 and spring member 442 are configured for rotational motion of direct wheel coupler 405 which translates to an opening and closing of the elevator platform by actuator wheel 404 within endoscope 402 during endoscope reprocessing. In another related embodiment, as illustrated in FIG. 3A, connecting rod 440 and spring member 442 are configured for translational or rectilinear motion of direct wheel coupler 405, which effects movement of the elevator during AER cleaning.

Figure 4A:
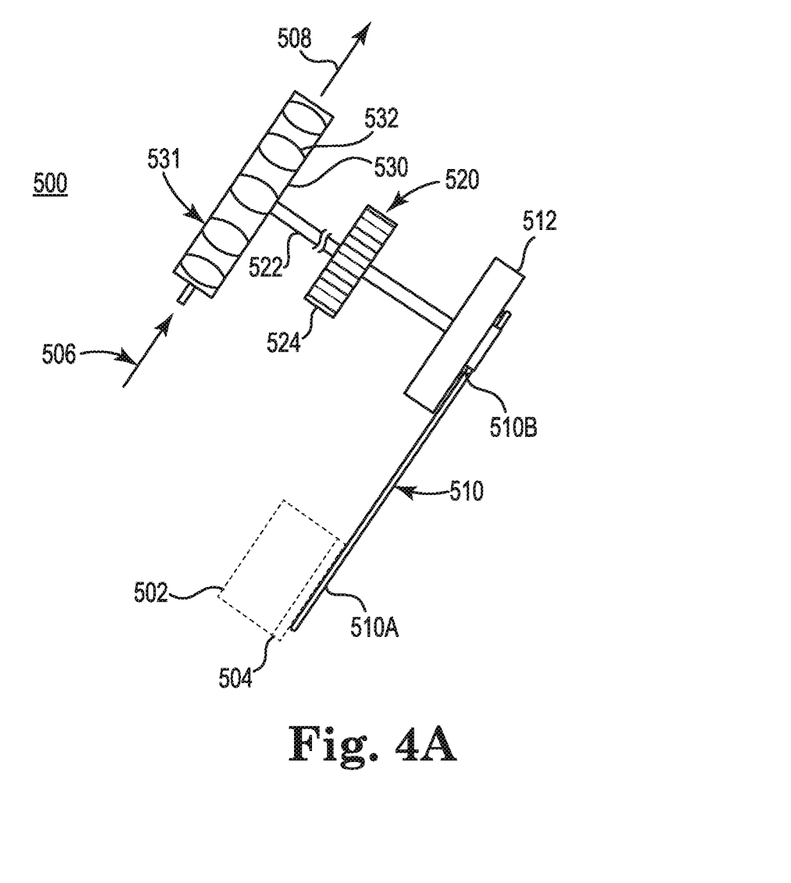
FIGS. 4A-4C illustrate perspective, side and front views of a first and second embodiments of turbine drive mechanisms, respectively, that drive the actuator lever of the elevator in the duodenoscope using the fluid flow of the AER and transitioning through a reduction stage to an actuator wheel connected to a shaft or rod coupled to a scope elevator actuator.

Referring now to FIG. 4A there is illustrated a perspective view of a turbine drive manipulator mechanism 500 that drives an actuator lever of an elevator in an endoscope or a duodenoscope 502, with the motive force on mechanism 500 being a cleansing fluid flow of an AER (not shown), and transitioning through a reduction stage to an actuator wheel 504 connected to a rod or shaft coupled to the endoscope elevator actuator. In this example embodiment, manipulator mechanism 500 using a turbine drive includes a direct wheel coupler 510 having a first coupler end 510A that engages actuator wheel 504 so as to rotate the actuator wheel axially upon actuation. Mechanism or assembly 500 also includes a gear assembly 520 mechanically coupled to a second coupler end 510B of the direct wheel coupler 510 via a wheel 512, gear assembly 520 imparting a rotational force to direct wheel coupler 510. Assembly 500 further includes a fluid turbine member 530 coupled via a surface 531 to shaft 522 and then to gear assembly 520 (directly here but optionally via another gear coupled to shaft 522) opposite direct wheel coupler 510, fluid turbine member 530 having a plurality of blades 532 disposed within a body of the fluid turbine member 530 and configured to rotate axially in a direction (arrow 506) of the cleansing fluid flowing 506 (providing the motive force) across plurality of blades 532, turbine member 530 imparting a rotational force to gear assembly 520 from a motive force 508 generated by the cleansing fluid flow, wherein the rotating motion on the direct wheel coupler translates to an opening and closing of the elevator platform by actuator wheel 504 within endoscope 502 during endoscope reprocessing. In a related embodiment, the gear assembly 520 is a gear reduction assembly. In various embodiments, the gear assembly or gear drive is replaced by a drive belt or drive band.

Figure 4B:
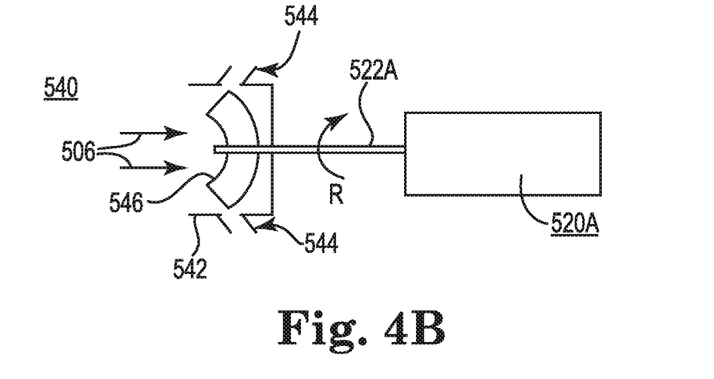
Figure 4C:
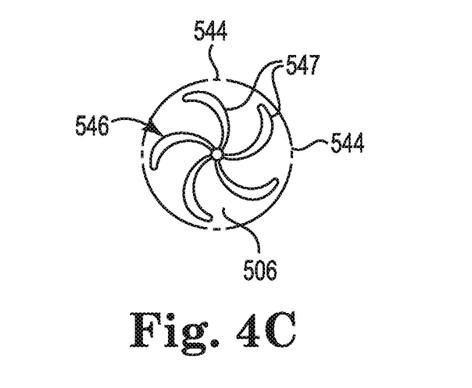

Referring now to FIGS. 4B and 4C, there is illustrated another turbine assembly 540, side and front views respectively. In particular, turbine assembly 540 includes a housing 542 having fluid flow outlets 544 and a blade assembly 546 supported therein. As fluid flow 506 flows through housing 542, a plurality of blades 547 move and drive shaft 522A with the fluid flowing out outlets 544. Output shaft 522A drives a gear assembly 520A, which can be a gear reduction assembly comprised of a parallel or offset drive train configuration.

Figure 5A:
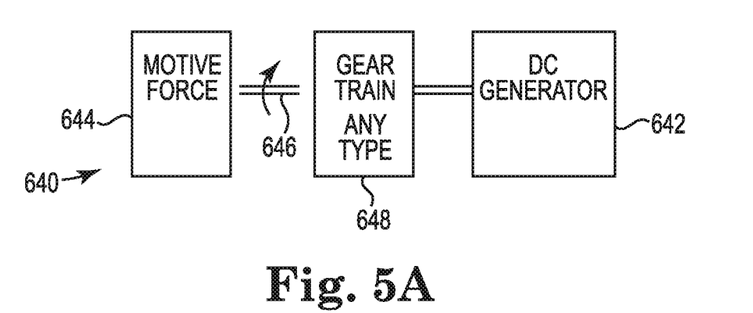
FIGS. 5A and 5B illustrate a system diagram and a perspective view of an embodiment of solenoid drive mechanism that utilizes fluid flow from the AER to convert the fluid flow as a motive force to electric current to then drive a solenoid that actuates the actuator lever on a duodenoscope.
Figure 5B:
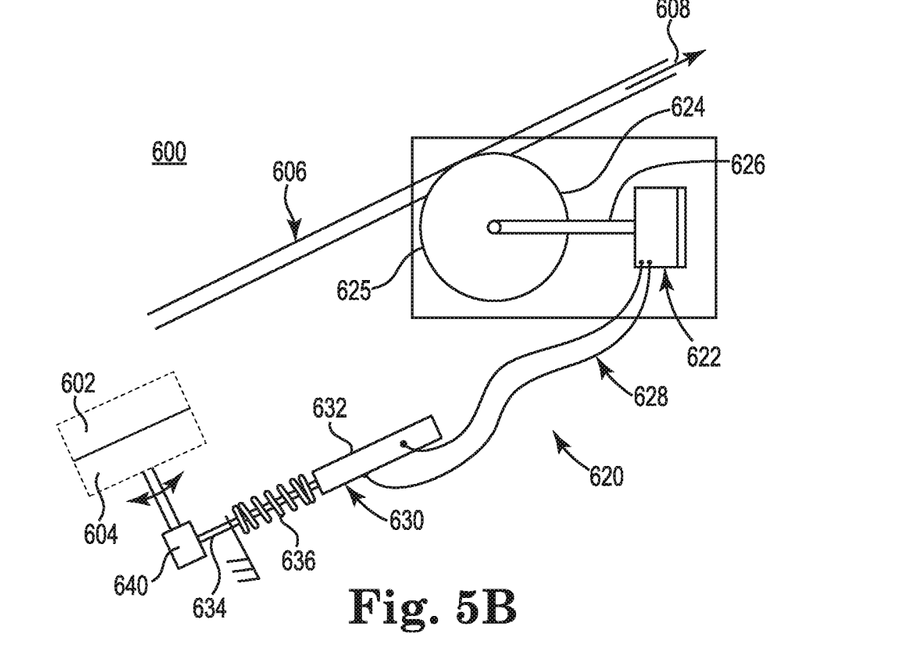
Figure 5C:
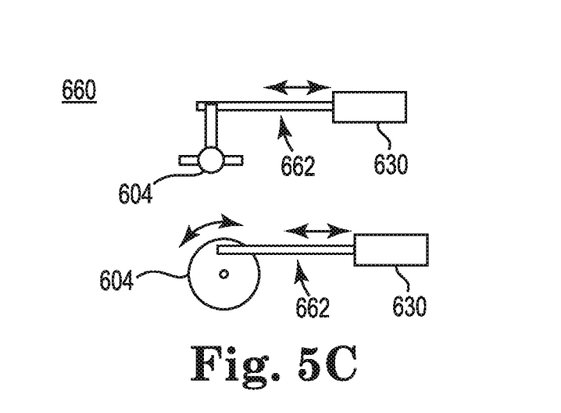
FIG. 5C illustrates side and top views, respectively, of another embodiment of part of a turbine drive mechanism utilizing a lever linkage configuration coupling between a solenoid assembly and an actuator wheel of the endoscope for translating movement from the solenoid assembly through to the actuator wheel.

Referring now to FIGS. 5A, 5B and 5C there are illustrated a system diagram and perspective, side and top views of two embodiments of a solenoid drive based manipulator mechanism 600 which use the cleansing fluid flow 606 from an AER (not shown) to convert a motive energy or force 608 from the flowing cleansing fluid (including a cleansing gas) within the AER to drive a small generator assembly 620. System 640 generally illustrates an elevator manipulator system for cleaning an elevator of an endoscope by harnessing the motive force of the cleansing fluid via a water wheel or turbine assembly 644 which in turns rotates a shaft 646 which is coupled to a gear train 648 (of any type, including a parallel or offset drive train). Gear train 648 is coupled to a DC generator 642 and through the rotational force imparted on gear train 648; generator 642 generates electric current that can be used to actuate a device that moves an actuator wheel in an endoscope that is coupled to the elevator mechanism.

Referring now to FIG. 5B, there is illustrated an actual manipulator assembly 600 that actually converts a motive force in the form of the cleansing fluid into electric current which then drives a solenoid assembly 630 that actuates an actuator lever 604 on the duodenoscope or endoscope 602. The endoscope accessory manipulator assembly 600 includes a fluid turbine member 624 having a plurality of blades 625 (partially shown) disposed within a body of the fluid turbine member and configured to rotate axially in a direction of the cleansing fluid flowing (arrow 608) across the plurality of blades, turbine member 624 imparting a rotational force to a connecting rod 626 protruding from a center axis of the turbine member from a motive force generated by the cleansing fluid flow to a direct current (DC) generator 622 coupled to connecting rod 626 from fluid turbine member 624. DC generator 622 includes two electrical leads 628 for transmitting DC current generated by the generator to a solenoid device assembly 630.

Solenoid assembly 630 includes a housing 632 and a plunger rod 634 disposed therein and protruding partially therefrom. Plunger rod 634 includes a spring member 636, located concentrically about plunger rod 634 and adjacent housing 632, and a connector 640 on a distal end which connects to actuator 604 of endoscope 602. Solenoid device 630 is electrically connected to the two electrical leads of the DC generator and moves plunger rod 634 in and out of housing 632 upon being energized by the DC current. The movement of plunger rod 634 along with spring member 636 and connector 640 impart an actuating force (arrow between 640 and 604) on the actuator wheel or member 604 of the endoscope, thereby controlling and manipulating the elevator or forceps device to release tissue and human or mammal debris during endoscope reprocessing. In this example embodiment, the plunger rod within the housing of the solenoid device is configured for translational or rectilinear motion and the compressed spring member returns the plunger rod to an extended configuration. In a related embodiment, a linear to angular motion converter of any type can be used at connector 640. In a related embodiment, the plunger rod within the housing of the solenoid device assembly is configured for rotational motion and the spring member is configured with a rotated torsion configuration so as to unwind and rotate the plunger rod to a neutral or a starting position.

Referring now to FIG. 5C, there is illustrated side and top views of a lever linkage configuration 660 coupling between solenoid assembly 630 and the actuator wheel 604 of the endoscope for translating movement with a lever linkage 662 from the solenoid assembly through to the actuator wheel.

The endoscopic procedures include herein, but are not limited to, the following known procedures and related endoscopic devices used therewith: gastroscopy, sigmoidoscopy and colonoscopy, esophagogastro duodenoscopy (EGD), endoscopic retrograde cholangiopancreatography (ERCP), and bronchoscopy.

The following patents and publications are incorporated by reference in their entireties: U.S. Pat. Nos. 3,934,820; 7,901,349; 8,109,872; 8,821,807; 9,033,867 and 9,995,268.

While the invention has been described above in terms of specific embodiments, it is to be understood that the invention is not limited to these disclosed embodiments. Upon reading the teachings of this disclosure many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

The invention claimed is:

1. An endoscope accessory assembly for use with an endoscope during processing with a cleansing fluid in an automatic endoscope reprocessing apparatus, the endoscope having an actuator wheel rotatable axially about a center axis within the endoscope so as to operate an elevator platform or forceps raiser device located at a distal end of the endoscope, the endoscope accessory assembly comprising:
- a direct wheel coupler having a first coupler end configured to engage the actuator wheel and to rotate the actuator wheel axially upon actuation;
- a gear assembly mechanically coupled to a second coupler end of the direct wheel coupler, the gear assembly configured to impart a rotational force to the direct wheel coupler; and
- a fluid turbine member coupled to the gear assembly opposite the direct wheel coupler, the fluid turbine member having a plurality of blades disposed within a body or housing of the fluid turbine member and configured to rotate perpendicularly to a direction of the cleansing fluid flowing across the plurality of blades, the turbine member imparting a rotational force to the gear assembly from a motive force generated by the cleansing fluid flow, wherein the rotating motion on the direct wheel coupler translates to an opening and closing of the elevator platform by the actuator wheel within the endoscope during endoscope reprocessing.

2. The endoscope accessory of claim 1, the gear assembly further comprising a connecting shaft or rod assembly coupled from a first gear of the gear assembly to a surface of the fluid wheel, the connecting rod assembly transferring rotational motion to the first gear of the gear assembly.

3. The endoscope accessory of claim 1, the gear assembly further comprising a connecting shaft or rod assembly coupled to a surface of the fluid wheel, the connecting rod assembly configured to convert rotational motion about the surface of the fluid wheel to linear motion on first gear of the gear reduction assembly.

4. The endoscope accessory of claim 1, wherein the gear assembly is a gear reduction assembly.

5. An endoscope accessory assembly for use with an endoscope during processing with a cleansing fluid in an automatic endoscope reprocessing apparatus, the endoscope having an actuator wheel rotatable axially about a center axis within the endoscope so as to operate an elevator platform or forceps raiser device located at a distal end of the endoscope, the endoscope accessory assembly comprising:
- a fluid turbine member having a plurality of blades disposed within a body of the fluid turbine member and configured to rotate perpendicularly to a direction of the cleansing fluid flowing across the plurality of blades, the turbine member imparting a rotational force to a connecting shaft or rod protruding from a center axis of the turbine member from a motive force generated by the cleansing fluid flow;
- a direct current (DC) generator coupled to the connecting shaft or rod from the fluid turbine member, the DC generator having two electrical leads for transmitting DC current generated by the generator; and
- a solenoid device assembly including a housing and a plunger rod disposed therein and protruding partially therefrom, the plunger rod having a spring member located concentrically about the plunger rod and adjacent the housing, the solenoid device electrically connected to the two electrical leads of the DC generator and configured to move the plunger rod in and out of the housing upon being energized by the DC current, wherein the movement of the plunger rod along with the spring member impart an actuating force on the actuator wheel of the endoscope controlling the elevator or forceps device during endoscope reprocessing.

6. The endoscope accessory of claim 5, wherein the plunger rod within the housing of the solenoid device assembly is configured for rotational motion and the spring member is configured with a rotated torsion configuration so as to unwind and rotate the plunger rod to a neutral or a starting position.

7. The endoscope accessory of claim 5, wherein the plunger rod within the housing of the solenoid device is configured for translational or rectilinear motion and the compressed spring member returns the plunger rod to an extended configuration.

8. An endoscope accessory assembly for use with an endoscope during processing with a cleansing fluid in an automatic endoscope reprocessing apparatus, the endoscope having an actuator wheel rotatable axially about a center axis within the endoscope so as to operate an elevator platform or forceps raiser device located at a distal end of the endoscope, the endoscope accessory assembly comprising:
- an impact head assembly having an impact head member disposed on a connecting shaft or rod member in a T-configuration, the connecting shaft or rod having a spring member located concentrically about a lower portion of the rod, the spring member configured to allow a predetermined at least one of an axial rotational and linear movement of the impact head assembly upon the impact head member being subjected to a rotational or linear force from a motive force generated by the cleansing fluid flow;
- a ratchet member operatively coupled with the connecting rod of the impact head assembly, the ratchet member including a predetermined number of indentations configured to engage a pin protruding laterally from the connecting rod that maintains the impact head member in a first position, the pin advancing progressively through the indentations as the impact head member is subjected to the motive force until the indentations terminate and the ratchet member releases the impact head assembly such that the impact head member moves to a second position, the rotational movement of the impact head assembly to the second position imparting a rotational or linear force on a distal end of the connecting rod; and
- a direct wheel coupler having a first coupler end configured to engage the connecting rod and a second end configured to engage the actuator wheel and rotate the wheel axially upon receiving an actuation force, wherein the movement of the connecting rod along with the spring member impart an actuating force on the actuator wheel of the endoscope controlling the elevator or forceps device during cleansing of the endoscope, wherein the rotating or linear motion on the direct wheel coupler translates to an opening and closing of the elevator platform by the actuator wheel within the endoscope during endoscope reprocessing.

9. The endoscope accessory of claim 8, wherein the connecting rod and the spring member are configured for rotational motion of the direct wheel coupler.

10. The endoscope accessory of claim 8, wherein the connecting rod and the spring member are configured for translational or rectilinear motion of the direct wheel coupler.

11. The endoscope accessory of claim 8, wherein the motive force is generated by a pressurized cleansing gas.

* * * * *